United States Patent
Walter et al.

(10) Patent No.: US 8,512,651 B2
(45) Date of Patent: Aug. 20, 2013

(54) APPARATUS AND METHOD FOR IDENTIFYING AT LEAST ONE SPECIMEN SLIDE

(75) Inventors: Roland Walter, Rellingen (DE); Christoph Schmitt, Schrieshelm (DE)

(73) Assignee: Leica Biosystems Nusslock GmbH, Nussloch (DE)

( * ) Notice: Subject to any disclaimer, the term of this patent is extended or adjusted under 35 U.S.C. 154(b) by 643 days.

(21) Appl. No.: 12/569,394

(22) Filed: Sep. 29, 2009

(65) Prior Publication Data

US 2010/0086964 A1    Apr. 8, 2010

(30) Foreign Application Priority Data

Oct. 6, 2008 (DE) .......................... 10 2008 050 525

(51) Int. Cl.
*A61B 10/00* (2006.01)

(52) U.S. Cl.
USPC ............... 422/536; 422/63; 422/64; 422/65; 422/66; 422/67; 347/102

(58) Field of Classification Search
USPC .............................. 422/64–67, 536; 347/102
See application file for complete search history.

(56) References Cited

U.S. PATENT DOCUMENTS

| | | | | |
|---|---|---|---|---|
| 6,715,870 | B2 * | 4/2004 | Kiene et al. | 347/102 |
| 2002/0167577 | A1 * | 11/2002 | Kiene et al. | 347/102 |
| 2004/0253662 | A1 | 12/2004 | Heid et al. | |
| 2005/0235542 | A1 | 10/2005 | Metzner et al. | |
| 2008/0220469 | A1 | 9/2008 | Heid et al. | |

FOREIGN PATENT DOCUMENTS

| | | |
|---|---|---|
| DE | 19841554 | 3/2000 |
| DE | 10154843 | 5/2003 |
| DE | 202004006265 | 7/2004 |

\* cited by examiner

*Primary Examiner* — Jyoti Nagpaul
(74) *Attorney, Agent, or Firm* — Schlee IP International, P.C.; Alexander R. Schlee

(57) ABSTRACT

An apparatus and method for tagging a specimen slide are described. The apparatus comprises a receiving region for receiving at least one cassette magazine, a reading unit for reading the machine-readable coded information of a cassette identifier of a cassette, and a tagging unit for generating a machine-readable coded information for tagging the specimen slide with a specimen slide identifier that depends on the cassette identifier. Data are transferred from the microtome to the apparatus via the data transfer path as soon as the cassette is inserted into the microtome, and only then can the machine-readable coded information for tagging the specimen slide be applied onto the specimen slide by the tagging unit.

11 Claims, 2 Drawing Sheets

APPARATUS AND METHOD FOR IDENTIFYING AT LEAST ONE SPECIMEN SLIDE

CROSS-REFERENCE TO RELATED APPLICATION

This application claims the priority of the German patent application DE 102008050525.0 having a filing date of Oct. 6, 2008. The entire content of this prior German patent application DE 102008050525.0 is herewith incorporated by reference.

BACKGROUND OF THE INVENTION

The invention relates to an apparatus for identifying at least one specimen slide. The apparatus has at least one reading unit for reading a machine-readable coded information of a cassette identifier of a cassette, and at least one tagging unit for generating an at least machine-readable coded information for identifying the specimen slide. Identification of the specimen slide is accomplished with a specimen slide identifier dependent on the cassette identifier sensed with the aid of the reading unit. The invention further relates to a method for identifying at least one specimen slide.

The apparatus and the method are preferably used in histological technology. In histological technology, tissue samples that were taken from a patient are investigated. For this, the tissue samples are firstly embedded into an embedding medium, preferably paraffin. A hardened paraffin block produced in this fashion, having the tissue sample, is also referred to as a sample block. The sample blocks are each arranged in a cassette, and are transported and processed in that cassette. For unique identifiability of the sample blocks, the cassettes each have a unique identifier. The sample blocks are preferably delivered to a microtome, in which thin sections of the sample blocks are produced. The thin sections are each mounted onto a specimen slide, stained, and covered with a coverslipping agent and a coverslip. The specimens are then delivered for further investigations to at least one further apparatus, in particular to a microscope.

The tissue samples, and thus also the thin sections that are produced, must be uniquely identifiable throughout all the processing steps that have been described. The intention thereby is to preclude confusion between the samples in order to prevent incorrect allocation of a sample, a thin section, or an investigation result. An incorrect allocation can cause a healthy patient to be considered ill, and an ill patient to be erroneously considered healthy. Medical actions that might be necessary are then omitted or are instituted only after a delay. Unique identification further serves to avoid sample losses, and to re-locate samples that have been lost. In order to ensure unique identifiability of the samples during the entire processing procedure, the specimen slides onto which the thin slides of the tissue samples are mounted are equipped with a unique identifier. The two methods explained below are, in particular, conceivable for this:

In the first possible method, the cassettes rest individually on a cooling plate. Upon insertion of a cassette into a microtome, the identifier of the cassette is read out. As a function of that identifier, at least one specimen slide is manually labeled. Such manual labeling is susceptible to error by its very nature. In addition, such manual labeling is time- and cost-intensive. Manual identification of the specimen slides is particularly critical when the specimen slides must be read by other persons in the context of later method steps, since confusion can easily occur if the handwriting is unclear.

In a second possible method, the specimen slides are already identified before the cassettes are delivered to the microtome. The identified specimen slides, and the cassettes having the tissue samples, are transported individually to the microtome. Once one or more thin sections have been produced from a tissue sample with the aid of a microtome, the pre-identified specimen slides belonging to the cassette having the microtomed sample block must then be laboriously searched for manually, and identified by manual comparison of the identifier. This in turn carries the risk of confusion, and is moreover time- and cost-intensive.

Also known, from the document DE 101 54 843 A1, are a method and an apparatus for identifying specimen slides of microtomed tissue samples, and for processing them. In the method, an identifying information belonging to a slide is automatically sensed while it is being arranged in a microtome, and an identifier allocated thereto is automatically transferred onto at least one specimen slide. At the point in time at which a microtomed tissue sample must be mounted onto a specimen slide, only that specimen slide which is equipped with the identifier is presented at the microtome workstation. The apparatus described comprises a microtome and an identifying device arranged next to the microtome. The slides having the tissue samples to be microtomed are delivered individually to the microtome. The apparatus is disadvantageous in that clarity and the level of organization at the workstation are limited by the individual delivery of the slides having the tissue sample, thereby increasing the probability of error.

The document DE 198 41 554 A1 discloses an apparatus for receiving solid or liquid sample material, in which a coding fixedly joined to the apparatus, and/or a memory element, are provided. The codings, or the codes stored in the memory elements, are different for any two apparatuses.

SUMMARY OF THE INVENTION

The object of the invention is to describe an apparatus for identifying specimen slides that ensures simple and reliable identification of the specimen slides and simple, clearly organized handling of cassettes in which are contained sample blocks from which thin sections to be mounted onto the specimen slides are to be prepared.

This object is achieved by an apparatus for tagging at least one specimen slide, said apparatus comprising: at least one receiving region for receiving at least one cassette magazine having at least one cassette, the cassette having a cassette identifier having at least one machine-readable coded information item; a removal unit for removing a cassette from the cassette magazine; at least one reading unit for reading the machine-readable coded information of the cassette identifier of a cassette; and at least one tagging unit for generating an at least machine-readable coded information for tagging the specimen slide with a specimen slide identifier that depends on the cassette identifier read by the reading unit; wherein the apparatus is adapted to be connected via at least one data transfer path to a microtome; and data are transferred from the microtome to the apparatus via the data transfer path as soon as the cassette is inserted into the microtome, and only then can the machine-readable coded information for tagging the specimen slide be applied onto the specimen slide by the tagging unit.

This object is further achieved by a method of tagging at least one specimen slide, comprising: removing a cassette from a cassette magazine by a removal unit, said cassette having a cassette identifier having at least one machine-readable coded information; reading the machine-readable coded information of the cassette identifier of the cassette by at least one reading unit at a point in time of one of before, during, and after removal of the cassette from the cassette magazine; generating by at least one tagging unit a specimen slide identifier that interrelates to the cassette identifier read by the reading unit, said tagging unit generating an at least machine-readable coded information for identification of the specimen slide; inserting the cassette into a microtome; transferring data from a microtome to the apparatus via a data transfer path as soon as the cassette has been inserted into the microtome; enabling tagging of the specimen slide by the tagging unit by applying the machine-readable coded information for identifying the specimen slide onto the specimen slide only after having transferred data from the microtome to the apparatus; and tagging the specimen slide by the tagging unit by applying the machine-readable coded information for identifying the specimen slide onto the specimen slide.

What is achieved by way of such an apparatus is that the specimen slide is identified in confusion-proof fashion with a specimen slide identifier having a machine-readable coded information item, the specimen slide identifier being dependent on the cassette identifier, sensed with the aid of a reading unit, of the cassette. Clearly organized handling of the cassettes is additionally achieved, since the cassettes are stored in a cassette magazine upon delivery to the apparatus, the cassette magazine being receivable by a receiving region of the apparatus. The risk of error and confusion can be further reduced thereby.

It is advantageous to identify the specimen slide only with a specimen slide identifier that is dependent on the cassette identifier of a cassette removed from the cassette magazine with the aid of a removal unit. The risk of confusion of specimen slides can thereby be further reduced, since the identified specimen slides are uniquely allocatable to the removed cassette.

It is further advantageous if the machine-readable coded information for identification of the specimen slide comprises at least a portion of the information of the information coded in the cassette identifier. This makes it easier to allocate a specimen slide to a cassette.

It is particularly advantageous that the specimen slide identifier comprises the cassette identifier.

It is furthermore advantageous that the tagging unit identifies multiple specimen slides, each having a specimen slide identifier dependent on the cassette identifier sensed with the aid of the reading unit. It thereby becomes possible to produce, in one working operation, multiple specimen slides having thin sections of a sample block.

It is advantageous that the machine-readable coded information for identification of the specimen slide respectively comprises at least a portion of the information of the information coded in the cassette identifier, and the specimen slide identifier of each specimen slide respectively comprises an additional information for distinguishing between the specimen slides allocated to one cassette. The result is both that the specimen slides can be allocated uniquely to a cassette and thus to a sample block, and that the specimen slides can be distinguished from one another.

It is additionally advantageous to provide at least one specimen slide storage region in which multiple specimen slides are receivable. The specimen slides are automatically and individually removable from the specimen slide storage region and deliverable to the tagging unit. It is possible in this fashion to dispense with manual delivery of the specimen slides, thereby reducing working complexity and cost.

Removal of a cassette from the cassette magazine with the aid of the removal unit can be accomplished manually, semi-automatically, or fully automatically.

It is additionally advantageous that the apparatus comprises a cooling unit which cools the cassettes while the cassette magazine is arranged in the receiving region. Alternatively or additionally, the apparatus can have a thermal insulation system of the receiving region, in order to reduce heat exchange between a sample block present in a cassette of the cassette magazine and the environment. It is thereby possible on the one hand to achieve the optimum sectioning temperature for the sample block, and on the other hand to extend the holding time of the tissue sample.

It is additionally advantageous to provide a cassette output region for output of the cassette removed from the cassette magazine. It is particularly advantageous to connect the cassette output region to a microtome, and to deliver a cassette removed from the cassette magazine to the microtome automatically via the cassette output region. This ensures that the cassette removed from the cassette magazine is also in fact delivered to the microtome. Manual intervention in an automatic process of this kind is not necessary. This reduces the risk of confusion, since the only specimen slide made available by the apparatus for identifying specimen slides are those that are allocated to cassettes received in the microtome for processing.

It is additionally advantageous to connect the apparatus to a microtome via at least one data transfer path. Data are transferred from the microtome to the apparatus via this data transfer path as soon as the cassette is inserted into the microtome. Only then can the machine-readable coded information items for identifying the specimen slide be applied onto the specimen slide with the aid of the tagging unit. The result of this is that only specimen slides that are allocated to the cassette actually inserted in the microtome are made available by the apparatus for identifying the specimen slides. This reduces the risk of confusion.

It is additionally advantageous that the apparatus comprises at least one central database in which is stored the number of specimen slides that are to be identified for a respective cassette.

A further aspect of the invention relates to a method for identifying at least one specimen slide. A cassette having a cassette identifier having at least one machine-readable coded information is removed from a cassette magazine with the aid of a removal unit. Before, during, or after removal of the cassette from the cassette magazine, the machine-readable coded information of the cassette identifier is sensed with the aid of at least one reading unit. A specimen slide identifier is then produced, as a function of the cassette identifier sensed with the aid of the reading unit, with the aid of at least one tagging unit for producing an at least machine-readable coded information for identification of the specimen slide.

The method specified by the independent method claim can be further developed in the same manner as the apparatus according to claim 1. The method can be further developed, in particular, with the features described in the dependent claims referenced back to the apparatus, or with corresponding method features.

Further features and advantages of the invention are evident from the description that follows, which explains the invention in further detail with reference to exemplifying embodiments and in conjunction with the appended Figures.

DETAILED DESCRIPTION OF THE DRAWINGS

Figure 1:
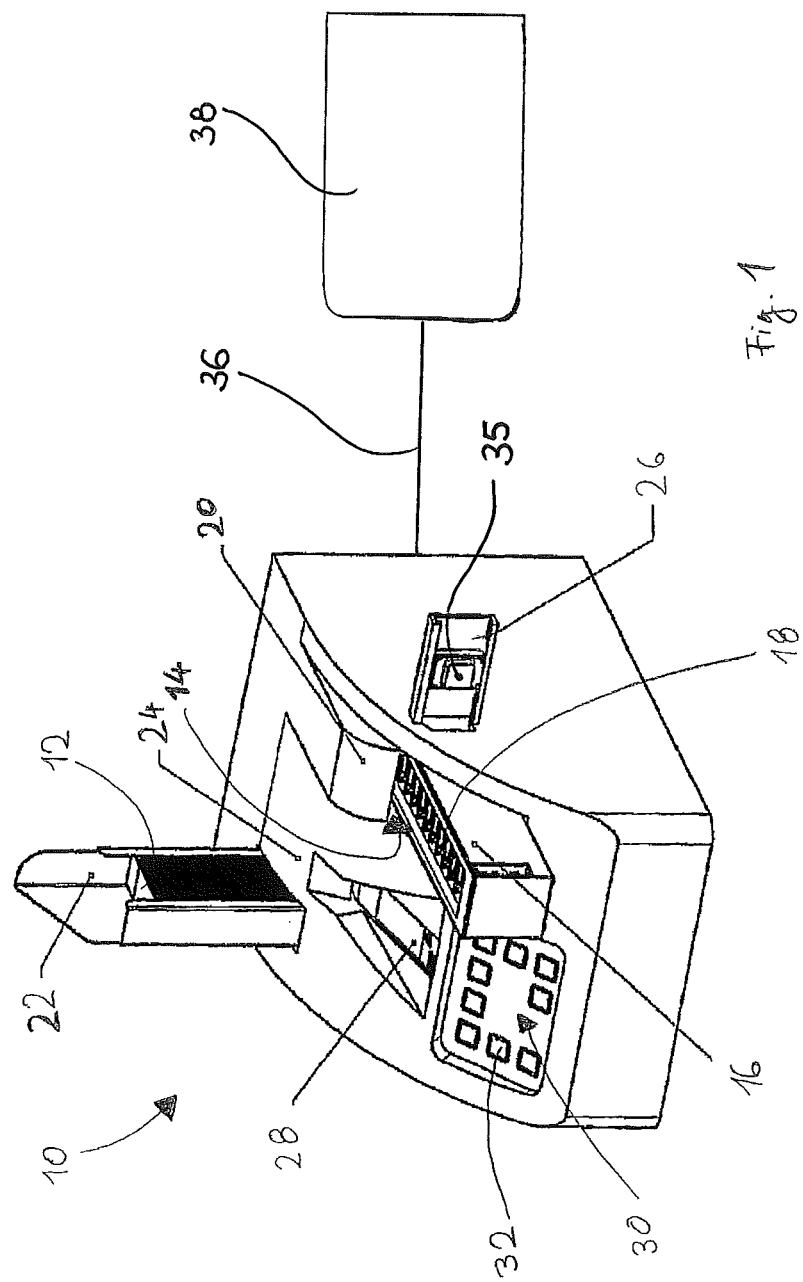
FIG. 1 is a schematic perspective depiction of an apparatus for identifying specimen slides, having a cassette magazine received in a receiving region.

FIG. 1 is a schematic perspective depiction of an apparatus 10 for identifying specimen slides 12, having a cassette magazine 16 received in a receiving region 14. Cassette magazine 16 has a plurality of cassette receiving regions. A cassette receiving region of this kind is also referred to as a "compartment." At least one cassette 18 is receivable in each cassette receiving region. One sample block 35 is arranged in each cassette 18.

Each sample block 35 comprises at least one sample, embedded in an embedding material. Paraffin, in particular, is used as an embedding material. The samples are, in particular, biological samples that were taken from a patient.

Cassettes 18 arranged in cassette magazine 16 each have a cassette identifier having an at least machine-readable coded information item. A written label, a bar code, and/or electrical components, preferably transponders and/or RFID tags, can be used for cassette identification. The cassette identifier serves for unique identification of cassette 18 and thus of the sample block 35 arranged in cassette 18. This is intended to prevent any confusion of sample blocks 35.

Apparatus 10 further has a removal unit (not depicted) for removing a cassette 18 from cassette magazine 16. The removal of a cassette 18 from cassette magazine 16 with the aid of the removal unit can occur manually, semi-automatically, or fully automatically. A semi-automatic removal unit functions autonomously, but some working steps are performed manually. In a fully automatic removal unit, all the working steps occur without manual intervention.

Apparatus 10 furthermore comprises a reading unit 20 for reading the machine-readable coded information of the cassette identifier of a cassette 18. Reading of the machine-readable coded information of the cassette identifier of cassette 18 can occur before, during, or after the removal of cassette 18 from cassette magazine 16.

Apparatus 10 furthermore has a specimen slide storage region 22 in which multiple specimen slides are receivable. One of the specimen slides is designated, by way of example, with the reference character 12. Specimen slides 12 are, individually and fully automatically, removable from specimen slide storage region 22 and deliverable to a tagging unit 24.

With the aid of tagging unit 24, an at least machine-readable coded information is produced for the identification of a specimen slide 12 with a specimen slide identifier dependent on the cassette identifier sensed with the aid of reading unit 20. The purpose of the specimen slide identifier is to allow a specimen slide 12 to be uniquely allocated to a cassette 18 and thus to the sample block 35 contained in cassette 18.

A specimen slide 12 is preferably identifiable only with a specimen slide identifier that is dependent on the cassette identifier of a cassette 18 removed from cassette magazine 16 with the aid of the removal unit. This ensures that identification of the specimen slide 12 with the specimen slide identifier does not occur until cassette 18 is removed from cassette magazine 16, so that only specimen slides 12 that have a specimen slide identifier that is allocated to the removed cassette 18 are made available for placement of a thin section.

Apparatus 10 further has a cassette output region 26 for outputting cassette 18 removed from cassette magazine 16, and a specimen slide output region 28 for outputting specimen slides 12 removed from specimen slide storage region 22 and identified with the aid of tagging unit 24. The fact that the removed cassette 18, and specimen slide 12 identified with a specimen slide identifier as a function of the cassette identifier of the removed cassette 18, are presented simultaneously at cassette output region 26 and specimen slide output region 28 for placement of a thin section, reduces the risk of erroneously not allocating a specimen slide 12 to the cassette 18 to which it was allocated.

Specimen slide identification can be accomplished, for example, by way of a written label, a code, and/or an electrical component, in particular transponders and/or RFID tags. The machine-readable coded information for the identification of specimen slide 12 advantageously comprises at least part of the information of the information coded by the cassette identifier.

Alternatively, it is possible for the specimen slide identifier to comprise the cassette identifier. If multiple specimen slides 12 are respectively identified, by tagging unit 24, with a specimen slide identifier dependent on a cassette identifier sensed with the aid of reading unit 20, it is advantageous for the machine-readable coded information for the identification of specimen slide 12 to comprise in each case at least part of the information of the information coded by the cassette identifier, and for the specimen slide identifier of each specimen slide 12 to comprise a respective additional information for differentiation between the specimen slides 12 allocated to a cassette 18. This can be accomplished, in particular, by the fact that the specimen slide identifier comprises the cassette identifier, and is additionally supplemented with a serial number.

Cassette output region 26 of apparatus 10 can be connected to a microtome 38. Cassette 18 that has been removed is automatically deliverable to the microtome via cassette output region 26.

Additionally or alternatively, apparatus 10 can be connected to the microtome via at least one data transfer path 36. Data are transferred from the microtome to apparatus 10, via the data transfer path, as soon as the cassette 18 removed from the cassette magazine 16 is inserted into the microtome. These data can be, in particular, authorization data. Only once these data have been transferred from the microtome to apparatus 10 can the machine-readable coded information items for the identification of specimen slide 12 be applied, with the aid of tagging unit 24, onto specimen slide 12. This ensures that only those specimen slides 12 whose specimen slide identifiers were produced as a function of the cassette identifier of cassette 18 inserted in the microtome are presented in specimen slide output region 28.

Apparatus 10 further has a control panel 30 having multiple operating elements. One of these operating elements is designated, by way of example, with the reference character 32. Operating personnel can operate apparatus 10 with the aid of operating elements 32 of control panel 30.

Apparatus 10 is connected to a database (not depicted) in which a definition is made as to how many specimen slides 12 are required for a respective cassette 18, and thus how many specimen slides 12 are to be identified with a specimen slide identifier with the aid of tagging unit 24. The database can be, in particular, a local database of apparatus 10, or a hospital database.

It is advantageous if output of a cassette 18 in cassette output region 26, and identification of the specimen slide 12 allocated to cassette 18, occur simultaneously. As a result, only those specimen slides 12 that are allocated to the sample block 35 currently being processed are available in specimen slide output region 28, and confusion with other cassettes or sample is precluded. New specimen slides 12 are outputted when a further cassette 18 has been removed from cassette magazine 16 and presented in output region 26.

In a further alternative embodiment, apparatus 10 has a cooling unit that cools cassette 18 while cassette magazine 16 is arranged in receiving region 14. Additionally or alternatively, apparatus 10 can comprise elements for thermal insulation of receiving region 14, in order to reduce heat exchange between a sample block 35 present in a cassette 18 of cassette magazine 16 and the environment. The optimum sectioning temperature of the sample block 35 can be ensured with the aid of the cooling unit and/or thermal insulation.

Figure 2:
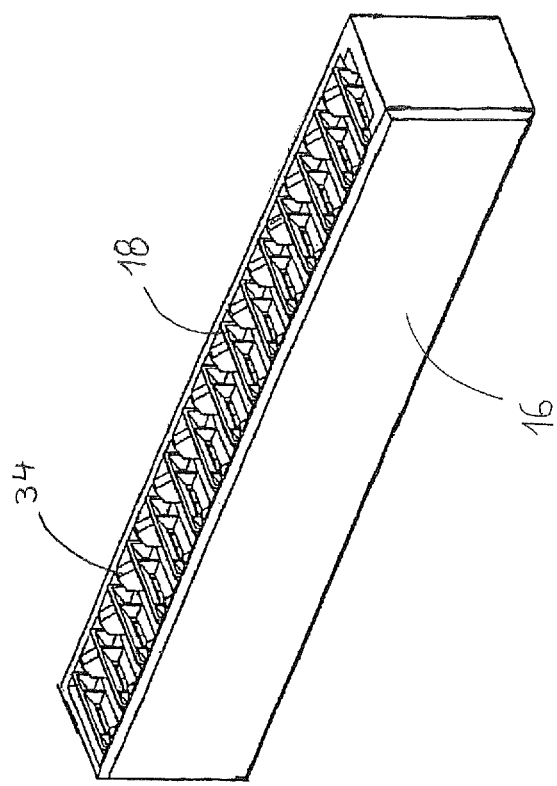
FIG. 2 is a schematic perspective depiction of a cassette magazine.

FIG. 2 is a schematic perspective depiction of a cassette magazine 16. Elements having the same configuration or the same function have the same reference characters.

The cassette receiving regions of cassette magazine 16 are each delimited by at least two delimiting elements and by the side walls of cassette magazine 16. One of these delimiting elements is designated, by way of example, with the reference character 34. The cassette receiving regions are dimensioned in such a way that exactly one cassette 18 can be received in each cassette receiving region.

LIST OF REFERENCE NUMERALS

10 Apparatus
12 Specimen slide
14 Receiving region
16 Cassette magazine
18 Cassette
20 Reading unit
22 Specimen slide storage region
24 Tagging unit
26 Cassette output region
28 Specimen slide output region
30 Control panel
32 Operating element
34 Delimiting element
35 Sample block
36 Data transfer path
38 Microtome

What is claimed is:

1. A system for cutting at least one thin section from a sample block that is arranged in a cassette and tagging at least one specimen slide such that it can be allocated to a specific sample block, said system comprising:
a microtome for cutting the at least one thin section from a sample block when the cassette is inserted into the microtome; and
an apparatus for tagging the at least one specimen slide such that it can be allocated to the sample block when the sample block is inserted into the microtome, said apparatus comprising:
at least one receiving region for receiving at least one cassette magazine having at least one cassette, the cassette having a cassette identifier having at least one machine-readable coded information;
a removal unit for removing a cassette from the cassette magazine;
a cassette output region that is connected to the microtome for releasing the cassette that has been removed from the cassette magazine and delivering the cassette automatically to the microtome;
at least one reading unit for reading the machine-readable coded information of the cassette identifier of a cassette;
at least one tagging unit for generating an at least machine-readable coded information for tagging the specimen slide with a specimen slide identifier that depends on the cassette identifier read by the reading unit; and
at least one data transfer path connecting the apparatus to the microtome, transferring data from the microtome to the apparatus when the cassette is inserted into the microtome, and enabling the tagging unit for tagging the at least one specimen slide with the machine-readable coded information when the cassette is inserted in the microtome.

2. The apparatus according to claim 1, wherein the specimen slide can be tagged only with a specimen slide identifier that depends on the cassette identifier of a cassette that has been removed from the cassette magazine by the removal unit.

3. The apparatus according to claim 1, wherein the machine-readable coded information for identification of the specimen slide comprises at least a portion of the information that is coded in the cassette identifier.

4. The apparatus according to claim 1, wherein the specimen slide identifier comprises the cassette identifier.

5. The apparatus according to claim 1, wherein the tagging unit tags multiple specimen slides, each having a specimen slide identifier that depends on the cassette identifier that is read by the reading unit.

6. The apparatus according to claim 5, wherein the respective machine-readable coded information for identification of the specimen slide comprises at least a portion of the information coded in the cassette identifier, and the specimen slide identifier of each specimen slide comprises additional information for distinguishing between the specimen slides allocated to one cassette.

7. The apparatus according to claim 1, further comprising at least one specimen slide storage region that is adapted to receive a plurality of specimen slides, the specimen slides being automatically and individually removable from the specimen slide storage region and deliverable to the tagging unit.

8. The apparatus according to claim 1, wherein a cassette from the cassette magazine is removable by the removal unit by at least one of manual removal, semi-automatic removal, and fully automatic removal.

9. The apparatus according to claim 1, further comprising a cooling unit that cools the cassettes while the cassette magazine is in the receiving region.

10. The apparatus according to claim 1, further comprising elements of a thermal insulation system of the receiving region for reducing heat exchange between a sample block present in a cassette of the cassette magazine and the environment.

11. The apparatus according to claim 1, further comprising at least one database storing the number of specimen slides that are to be tagged for a respective cassette.

* * * * *

UNITED STATES PATENT AND TRADEMARK OFFICE
CERTIFICATE OF CORRECTION

PATENT NO. : 8,512,651 B2
APPLICATION NO. : 12/569394
DATED : August 20, 2013
INVENTOR(S) : Roland Walter and Christoph Schmitt Page 1 of 1

It is certified that error appears in the above-identified patent and that said Letters Patent is hereby corrected as shown below:

On the Title page of the patent, item (73), the Assignee reads: Leica Biosystems Nusslock GmbH and should read: Leica Biosystems Nussloch GmbH Signed and Sealed this
Nineteenth Day of November, 2013

Teresa Stanek Rea
*Deputy Director of the United States Patent and Trademark Office*